US009681855B2

United States Patent
Abe

(10) Patent No.: US 9,681,855 B2
(45) Date of Patent: Jun. 20, 2017

(54) ULTRASONIC DIAGNOSTIC APPARATUS, ULTRASONIC IMAGE PROCESSING APPARATUS, AND ULTRASONIC IMAGE PROCESSING METHOD

(71) Applicant: Toshiba Medical Systems Corporation, Otawara-shi (JP)

(72) Inventor: Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/296,937

(22) Filed: Oct. 18, 2016

(65) Prior Publication Data

US 2017/0035393 A1    Feb. 9, 2017

Related U.S. Application Data

(62) Division of application No. 12/187,673, filed on Aug. 7, 2008, now Pat. No. 9,504,441.

(30) Foreign Application Priority Data

Aug. 10, 2007  (JP) .................................. 2007-209959

(51) Int. Cl.
*A61B 8/00*   (2006.01)
*A61B 8/08*   (2006.01)
*A61B 8/14*   (2006.01)

(52) U.S. Cl.
CPC .......... *A61B 8/5207* (2013.01); *A61B 8/0883* (2013.01); *A61B 8/14* (2013.01); *A61B 8/461* (2013.01); *A61B 8/5223* (2013.01)

(58) Field of Classification Search
CPC ......... A61B 8/08; A61B 8/0883; A61B 8/461; A61B 8/5207; A61B 8/14; A61B 8/5223
(Continued)

(56) References Cited

U.S. PATENT DOCUMENTS 5,669,387 A   9/1997  Mine
5,785,654 A   7/1998  Iinuma et al.
(Continued)

FOREIGN PATENT DOCUMENTS

JP   2004-529719      9/2004
JP   2006-141509 A    6/2006
(Continued)

OTHER PUBLICATIONS

Japanese Office Action mailed Apr. 24, 2012, in Japanese Patent Application No. 2007-209959 filed Aug. 10, 2007 (with English Translation).
(Continued)

*Primary Examiner* — Bo J Peng
(74) *Attorney, Agent, or Firm* — Oblon, McClelland, Maier & Neustadt, L.L.P.

(57) ABSTRACT

Using three-dimensional mapping images at different time phases obtained by mapping motion information, a peak value of motion information in a local region is retrieved in each of the time phases. On the basis of the result, a locus line or the like indicative of fluctuations with time in the local peak region is generated and displayed so as to be, for example, superimposed on a mapping image. By observing the locus line on the mapping image displayed, the observer can directly grasp the state of the space-time propagation of mechanical excitement of the heart.

21 Claims, 9 Drawing Sheets

(58) Field of Classification Search
USPC ........ 600/437, 438, 440–443, 450, 453, 456
See application file for complete search history.

(56) References Cited

U.S. PATENT DOCUMENTS

| | | | |
|---|---|---|---|
| 5,913,824 | A | 6/1999 | Ogasawara et al. |
| 6,245,017 | B1 | 6/2001 | Hashimoto et al. |
| 6,638,221 | B2 | 10/2003 | Abe et al. |
| 6,884,216 | B2 | 4/2005 | Abe et al. |
| 7,722,540 | B2 | 5/2010 | Abe et al. |
| 7,837,625 | B2 | 11/2010 | Abe |
| 2004/0096106 | A1 | 5/2004 | Demi et al. |
| 2005/0085729 | A1 | 4/2005 | Abe |
| 2005/0104020 | A1 | 5/2005 | Zhan |
| 2006/0058675 | A1 | 3/2006 | Olstad |
| 2006/0083416 | A1 | 4/2006 | Nishiura |
| 2007/0038087 | A1 | 2/2007 | Abe et al. |
| 2007/0112531 | A1 | 5/2007 | Zhan |
| 2008/0285819 | A1 | 11/2008 | Konofagou et al. |

FOREIGN PATENT DOCUMENTS

| | | |
|---|---|---|
| JP | 2007-44499 A | 2/2007 |
| JP | 2007-143606 | 6/2007 |
| WO | WO 2006056221 | 6/2006 |

OTHER PUBLICATIONS

Office Action issued Apr. 14, 2015 in Japanese Patent Application No. 2014-128618.

Japanese Office Action mailed Jan. 31, 2012, in Japanese Patent Application No. 2007-209959 filed Aug. 10, 2007 (with English Translation).

Masood Ahmad et al. "Contraction Front Mapping in Detection of Ischemia during Live 3-Dimensional Dobutamine Stress Echocardiogrpahy", Circulation, 2006; 114: II_612, American Hearth Association, Inc., 2006, two pages.

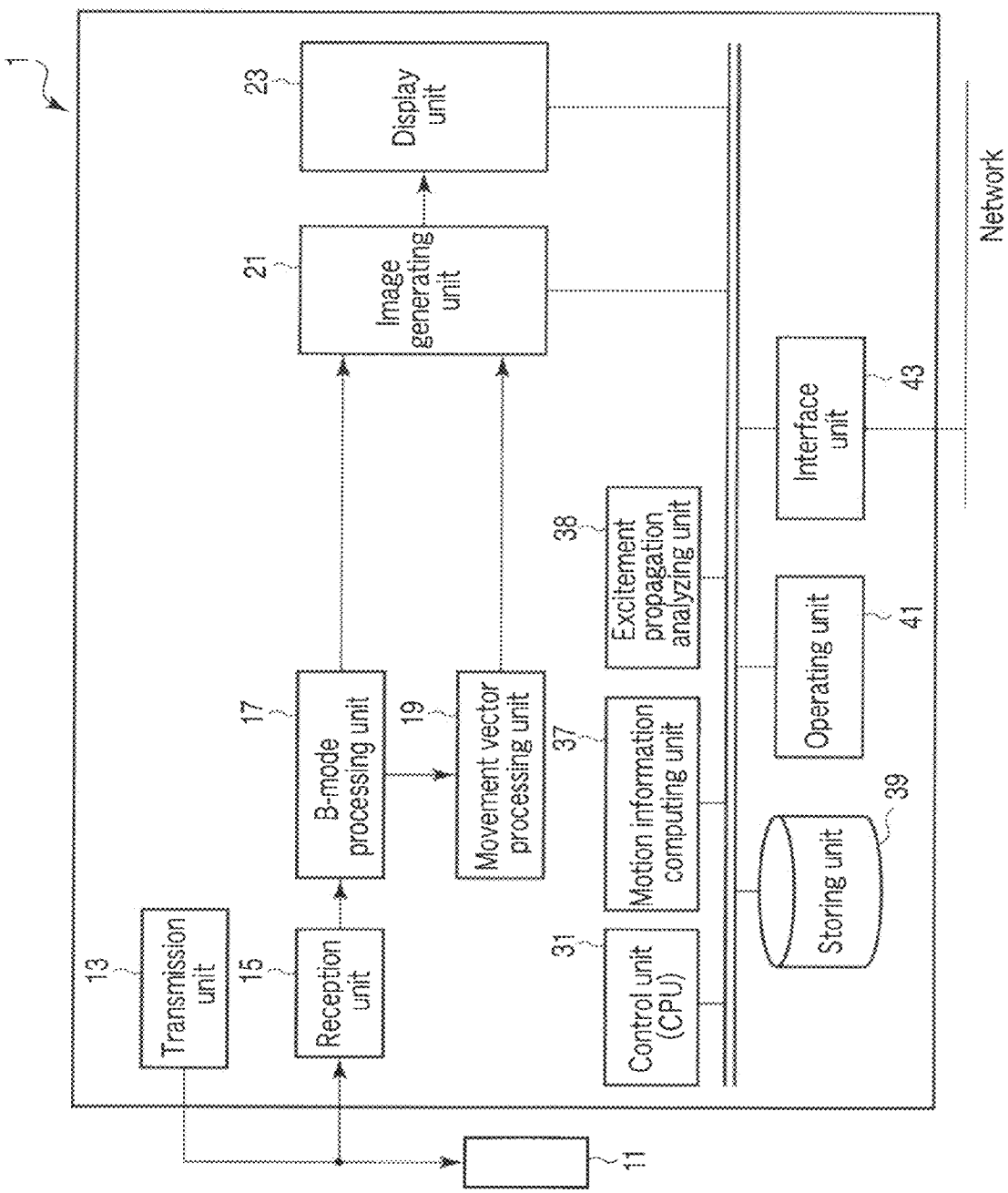
F I G. 1

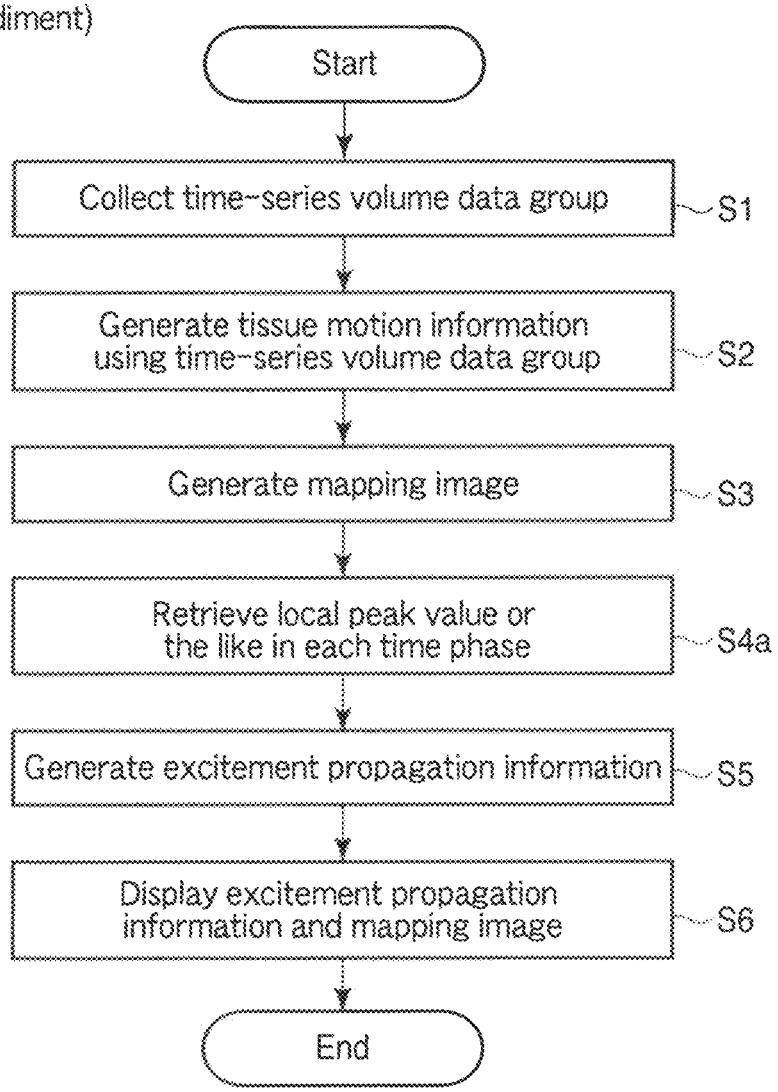
F I G. 2

ULTRASONIC DIAGNOSTIC APPARATUS, ULTRASONIC IMAGE PROCESSING APPARATUS, AND ULTRASONIC IMAGE PROCESSING METHOD

CROSS-REFERENCE TO RELATED APPLICATIONS

This application is a divisional of U.S. application Ser. No. 12/187,673 filed Aug. 7, 2008, and is based upon and claims the benefit of priority from prior Japanese Patent Application No. 2007-209959, filed Aug. 10, 2007, the entire contents of each of which are incorporated herein by reference.

BACKGROUND OF THE INVENTION

1. Field of the Invention

The present invention relates to an ultrasonic diagnostic apparatus and the like for providing information by which a state of a space-time change of mechanical excitement of a heart can be directly grasped and analyzable information using heart wall motion information analyzed three-dimensionally and for supporting diagnosis of mainly ischemia diseases.

2. Description of the Related Art

It is very important for diagnosis of body tissues such as cardiac muscle to objectively and quantitatively evaluate motions and functions of the body tissues. Also in image diagnosis using an ultrasonic image processing apparatus, various quantitative evaluations are attempted mainly on the heart as an example. For example, it is known that, in the contracting phase of normal cardiac muscle, the cardiac muscle is thickened in the radial direction (short axis) and is shortened in the longitudinal direction. Generally, it is said that the motion directions of thickening and shortening are orthogonal to each other, and the motions present different mechanisms. By observing the motions and evaluating the heart muscular wall motions, the possibility of diagnosis support on heart diseases such as myocardial infarction is suggested.

As a technique of displaying motion of the intimal surface of the heart or the like, for example, three-dimensional surface rendering display and, Bull's eye display (or polar-map display) are known. Typical examples include four-dimensional TSI (Tissue Synchronization Imaging) and CFM (Contraction Front Mapping). By using the methods, the state of a three-dimensional distribution on motion information of the heart wall can be observed quantitatively.

In studies in recent years, it is known that, for example, in diagnosis of ischemia disease and the like, it is effective to examine the state of space-time propagation of mechanical motion (mechanical excitement) as the pump of the heart.

However, by the conventional methods of displaying heart wall motion information, the state of space-time propagation of mechanical excitement cannot be directly grasped or quantified. For example, the purpose of the CFM is to grasp a deviation between regions at contraction peak timing, so that the state of space-time propagation of the heart wall motion cannot be directly grasped. For example, a technique disclosed in non-patent document 1 provides a distribution image of a certain region at the contraction peak in a time phase. Consequently, a deviation between regions at the contraction peak timing can be grasped, but the state of space-time propagation of the wall motion cannot be directly grasped.

BRIEF SUMMARY OF THE INVENTION

In view of the circumstances, an object of the present invention is to provide an ultrasonic diagnostic apparatus, an ultrasonic image processing apparatus, and an ultrasonic image processing method for providing information by which a state of a space-time propagation of mechanical excitement of a heart can be directly grasped and analyzed using heart wall motion information analyzed three-dimensionally and for supporting diagnosis of mainly ischemia diseases.

According to an aspect of the present invention, there is provided an ultrasonic diagnostic apparatus comprising: a motion information generating unit which generates first tissue motion information in a first period using first time as a reference, using a first volume data group made of a plurality of pieces of volume data collected in the first period, of cardiac tissue; an image generating unit which generates a first time-series tissue motion information image in the first period; a propagation information generating unit which generates first excitement propagation information showing a state of space-time propagation of mechanical excitement of the cardiac tissue by extracting a local area of the tissue motion information using the first time-series tissue motion information image; and a display unit which displays the first excitement propagation information.

According to another aspect of the present invention, there is provided an ultrasonic image processing apparatus comprising: a storing unit which stores first tissue motion information in a first period using first time as a reference, using a first volume data group made of a plurality of pieces of volume data collected in the first period, of cardiac tissue; an image generating unit which generates a first time-series tissue motion information image in the first period; a propagation information generating unit which generates first excitement propagation information showing a state of space-time propagation of mechanical excitement of the cardiac tissue by extracting a local area of the tissue motion information using the first time-series tissue motion information image; and a display unit which displays the first excitement propagation information.

According to yet another aspect of the present invention, there is provided an ultrasonic image processing method comprising: generating first tissue motion information in a first period using first time as a reference, using a first volume data group made of a plurality of pieces of volume data collected in the first period, of cardiac tissue; generating a first time-series tissue motion information image in the first period; generating first excitement propagation information showing a state of space-time propagation of mechanical excitement of the cardiac tissue by extracting a local area of the tissue motion information using the first time-series tissue motion information image; and displaying the first excitement propagation information.

BRIEF DESCRIPTION OF THE SEVERAL VIEWS OF THE DRAWING

FIG. 1 is a configuration diagram of an ultrasonic diagnostic apparatus 1 according to a first embodiment;

FIG. 2 is a flowchart showing the flow of processes executed in a process according to an excitement propagation information generating function (excitement propagation information generating process);

DETAILED DESCRIPTION OF THE INVENTION

Figure 3:
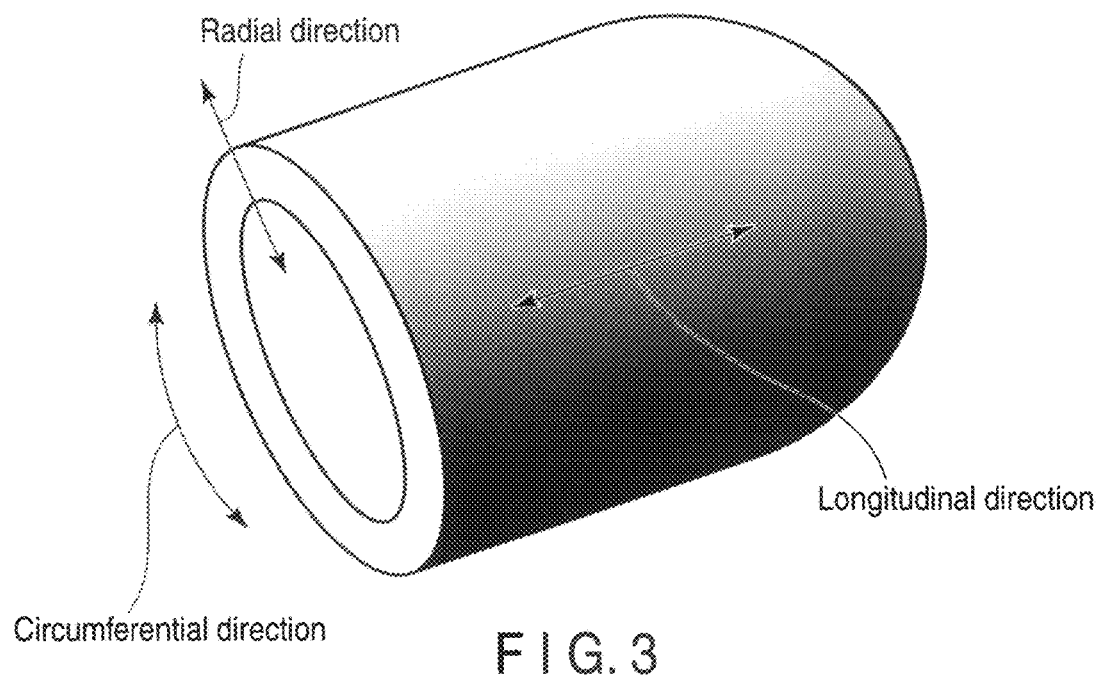
FIG. 3 is a diagram illustrating a radial direction, a longitudinal direction, and a circumferential direction of the heart.

First and second embodiments of the present invention will be described below with reference to the drawings. In the following description, the same reference numerals are designated to components having almost the same function and configuration, and repetitive description will be given only when needed.

In the following embodiments, the case of applying the technical idea of the present invention to an ultrasonic diagnostic apparatus will be described as an example. However, the invention is not limited to the case. The technical idea of the present invention can be also applied to an ultrasonic image processing apparatus such as a workstation, a personal computer or the like.

Components in the embodiments, particularly, a movement vector processing unit 19, a motion information computing unit 37, and an excitement propagation analyzing unit 38 (refer to FIG. 1) can be realized also by installing a software program for executing processes similar to those of the components into a computer such as a workstation, an ultrasonic diagnostic apparatus having a computer function, or the like and expanding the software program on a memory. A program capable of making the computer execute the method can be also stored in a recording medium such as a magnetic disk (a floppy (registered trademark) disk, a hard disk, or the like), an optical disk (CD-ROM, DVD, or the like), or a semiconductor memory and distributed.

(First Embodiment)

FIG. 1 is a configuration diagram of an ultrasonic diagnostic apparatus 1 according to a first embodiment. The ultrasonic diagnostic apparatus 1 includes an ultrasonic probe 11, a transmission unit 13, a reception unit 15, a B-mode processing unit 17, the movement vector processing unit 19, an image generating unit 21, a display unit 23, a control unit (CPU) 31, a trace processing unit 33, the volume data generating unit 35, a motion information computing unit 37, the excitement propagation analyzing unit 38, a storing unit 39, an operating unit 41, and a transmission/reception unit 43. In the case of applying the present invention to an ultrasonic image processing apparatus, the components in a dotted line in FIG. 1 are used.

The ultrasonic probe 11 has a plurality of piezoelectric vibrators for generating ultrasonic waves on the basis of a drive signal from the transmission unit 13 and converting reflection waves from a subject into electric signals, a matching layer provided for the piezoelectric vibrators, and a backing material or the like for preventing backward propagation of the ultrasonic waves from the piezoelectric vibrators. When the ultrasonic wave is transmitted from the ultrasonic probe 11 to the subject, various harmonic components are generated in propagation of the ultrasonic wave due to nonlinearity of a living tissue or the like. The fundamental waves and the harmonic components constituting transmission ultrasonic wave are backscattered by the boundary of acoustic impedance of a body tissue, micro scattering, or the like and are received as reflection wave (echo) by the ultrasonic probe 11.

The transmission unit 13 has a delay circuit, a pulsar circuit, and the like which are not shown. The pulsar circuit repetitively generates rate pulses for forming transmission ultrasonic waves at a predetermined rate frequency fr Hz (cycle: 1/fr second). The delay circuit gives delay time, which is necessary to converge the ultrasonic wave to a beam on the channel unit basis and to determine transmission directionality, to each of rate pulses. The transmission unit 13 applies a drive pulse to each of the vibrators so as to form an ultrasonic beam toward a predetermined scan line at a timing based on the rate pulse.

The reception unit 15 has an amplifier, an A/D converter, an adder, and the like which are not shown. The amplifier amplifies an echo signal taken via the probe 11 on the channel unit basis. The A/D converter gives delay time, which is necessary to determine reception directionality, to the amplified echo signal. After that, the adder performs an adding process. By the addition, an ultrasonic echo signal adapted to the predetermined scan line is generated.

The B-mode processing unit 17 generates a B-mode signal corresponding to intensity of amplitude of the ultrasonic echo by performing an envelope detection process on an ultrasonic echo signal received from the reception unit 15.

The movement vector processing unit 19 detects a movement position of a tissue using pattern matching process between two pieces of volume data of different time phases, and obtains the movement amount (or speed) of each tissue on the basis of the movement position. Concretely, as to a region of interest in one of the volume data pieces, a most analogous corresponding area in the other volume data is obtained. By obtaining the distance between the region of interest and the corresponding area, the movement amount of the tissue can be obtained. By dividing the movement amount by the time difference between the volumes, the movement speed of the tissue can be obtained. By performing the process volume by volume in each of positions on the volumes, a displacement (movement vector) of a tissue or space-time distribution data on displacement of the tissue can be obtained. The volume data is defined here as collection of reception signals having three-dimensional positional information (that is, collection of reception signals having spatial information).

The image generating unit 21 generates a B-mode ultrasonic image expressing a two-dimensional distribution of a predetermined cross section of a B-mode signal. On the basis of computed tissue motion information, the image generating unit 21 generates a two-dimensional image or three-dimensional image in which the motion information is mapped by using a method such as surface rendering or polar mapping.

The display unit 23 displays tissue motion information or the like as an image in a predetermined form on the basis of a video signal from the image generating unit 21. In the case of displaying a plurality of images, the display unit 23 displays a marker for supporting association of positions between images.

The control unit (CPU) 31 has the function of an information processor (computer) and controls the operation of the ultrasonic diagnostic apparatus body statically or dynamically. In particular, the control unit 31 realizes a tissue motion information displaying function which will be described later by expanding a dedicated program stored in the storing unit 39 to a not-shown memory.

The motion information computing unit 37 generates tissue motion information by time phase on the basis of the space-time distribution data output from the movement vector processing unit 19. The tissue motion information is physical information which can be obtained with respect to, for example, a displacement, velocity, strain, strain rate, rotation, rotation rate, and other tissue motion in a predetermined direction of a predetermined tissue such as a heart wall.

The excitement propagation information analyzing unit realizes an excitement propagation information generating function which will be described later.

The storing unit 39 is a recording medium such as a magnetic disk (a floppy (registered trademark) disk, a hard disk, or the like), an optical disk (CD-ROM, DVD, or the like), or a semiconductor memory and an apparatus for reading information recorded on the medium. The storing unit 39 stores transmission/reception conditions, a predetermined scan sequence, raw data and ultrasonic wave image data corresponding to each of time phases (for example, tissue image data captured in a tissue Doppler mode, a B mode, and the like), volume data of each time phase generated in advance, space-time distribution data related to a movement vector, a program for realizing the excitement propagation generating function which will be described later, diagnosis information (patient ID, remark of a doctor, and the like), a diagnosis protocol, a body mark generating program, and the like.

The operating unit 41 is connected to the apparatus body and has a mouse, a track ball, a mode change-over switch, a keyboard, and the like for performing various instructions from the operator, an instruction to set a region of interest (ROI), various image quality condition setting instructions, selection of arbitrary tissue motion information and arbitrary heat time phase in the excitement propagation generating function, and the like.

The interface unit 43 is an apparatus for analyzing information to/from another apparatus via a network. Data such as an ultrasonic image, analysis result, and the like obtained in the ultrasonic diagnostic apparatus 1 can be transferred to another apparatus via a network by the interface unit 43.

(Excitement Propagation Information Generating Function)

Next, the excitement propagation information generating function of the ultrasonic diagnostic apparatus 1 will be described. The function generates and provides information (excitement propagation information) by which a state of space-time propagation of mechanical excitement of the heart can be grasped directly using heart wall motion information analyzed three-dimensionally.

FIG. 2 is a flowchart showing the flow of processes executed in the process according to the excitement propagation information generating function (excitement propagation information generating process). Each of the processes will be described.

[Collection of Time-Series Volume Data: Step S1]

First, time-series volume data in a period of at least one heart beat (hereinbelow, called "time-series volume data group") at different collection times as references of a desired observation region in the heart or the entire heart of a patient, or the like is collected (step S1).

Specifically, volume data of a time series (of at least one heart beat) of a desired observation region in the heart of a patient is collected using a certain time "ti" as a reference and using a two-dimensional array probe from an apex cordis approach. The time "ti" as a reference is time information for identifying data collection time.

[Generation of Tissue Motion Information: Step S2]

Next, tissue motion information is generated (step S2). Specifically, the movement vector processing unit 19 extracts a cardiac muscle region on the basis of an instruction from the user or the like in volume data at a predetermined time phase, in volume data corresponding to the time phases of one heart beat or more constituting the collected time-series volume data group, tracks the extracted local cardiac muscle region with time by three-dimensional pattern matching process, and computes space-time movement vector information (step S2a). The motion information computing unit 37 computes heart wall motion information three-dimensionally using the computed space-time movement vector information, and generates a tissue motion information group constituted by the three-dimensional motion information of one or more heart beats (step S2b).

In the embodiment, to make explanation concrete, it is assumed that a tissue motion information group on a radial-strain is generated in the step S2. The example is illustrative, and the invention is not limited to the example. Examples of heart wall motion information to be generated include motion information (radial-strain or radial-strain rate) on a change in the radial direction, motion information (longitudinal-strain or longitudinal-strain rate) on a change in the longitudinal direction (for example, the direction of a tangent line of the long axis), motion information (circumferential-strain or circumferential-strain rate) on a change in the circumferential direction, motion information (rotation or rotation rate) on area gravity center in a short-axis plane, motion information (twist or twist rate) as the difference in rotations of different short-axis planes, motion information (torsion or torsion rate) obtained by normalizing the twist information with the distance between the short-axis planes, and motion information (displacement or velocity) on a motion distance. The radial direction, the longitudinal direction, and the circumferential direction are illustrated in FIG. 3. Generation of any of the heart wall motion information is determined by initial setting or a selecting operation from the operating unit 41.

[Generation of Motion Information Mapping Image: Step S3]

Subsequently, using the tissue motion information group, time-series mapping images obtained by mapping the motion information are generated (step S3). For example, using the tissue motion information group, the image generating unit 21 generates surface rendering images at different time phases by color-coding a radial strain on a change in the radial direction generated and mapping the codes to a region corresponding to the heart muscle. A method of mapping the tissue motion information is not limited to the surface rendering process. For example, as long as a list such as a polar map is displayed, any method can be used.

[Retrieval of Local Peak Value: Step S4a]

Next, retrieval of a local peak value at each of time phases is executed using the generated surface rendering images of a time series (that is, at time phases) (step S4a). Specifically, the excitement propagation analyzing unit 38 retrieves a region where the motion information has the maximal value (or minimal value) in the entire surface rendering image at initial time phase t0 selected by a predetermined method. The excitement propagation analyzing unit 38 sets a predetermined local area using, as a reference, the position corresponding to the region retrieved at the time phase t0 on the surface rendering image at the next time phase t1, and retrieves a region (the number of regions is not limited to one) having the maximal value or minimal value (local peak value) of motion information in the local area. Further, the excitement propagation analyzing unit 38 sets a predetermined local area using, as a reference, the position corresponding to the region retrieved at the time phase t1 on the surface rendering image at the time phase t2 next to the time phase t1, and retrieves a region having a local peak value in the predetermined area. After that, the local peak value is similarly retrieved from all of the time-series surface rendering images.

The excitement propagation information generating function is not particularly limited to the shape and size of a local area. However, it is preferable that the shape and size change according to, for example, the cardiac cycle, disease condition, and the like of the subject. For example, according to the motion velocity of a local area which is set at the initial time phase, the shape and size of the local area at the following time phases may be adaptively changed. The motion velocity of the local area can be calculated on the basis of the motion amount between time phases and the frame time intervals.

[Generation of Excitement Propagation Information: Step S5]

Next, using the retrieved local peak values at the time phases, the excitement propagation information is generated (step S5). Specifically, the excitement propagation analyzing unit 38 generates, as excitation propagation information, a locus line indicative of fluctuations with time of a region having a local peak value on the basis of the retrieved local peak values at the different time phases.

[Display of Excitation Propagation Information and Mapped Image: Step S6]

The control unit 31 controls the display unit 23 so as to display the excitation propagation information together with the mapping image.

Figure 4:
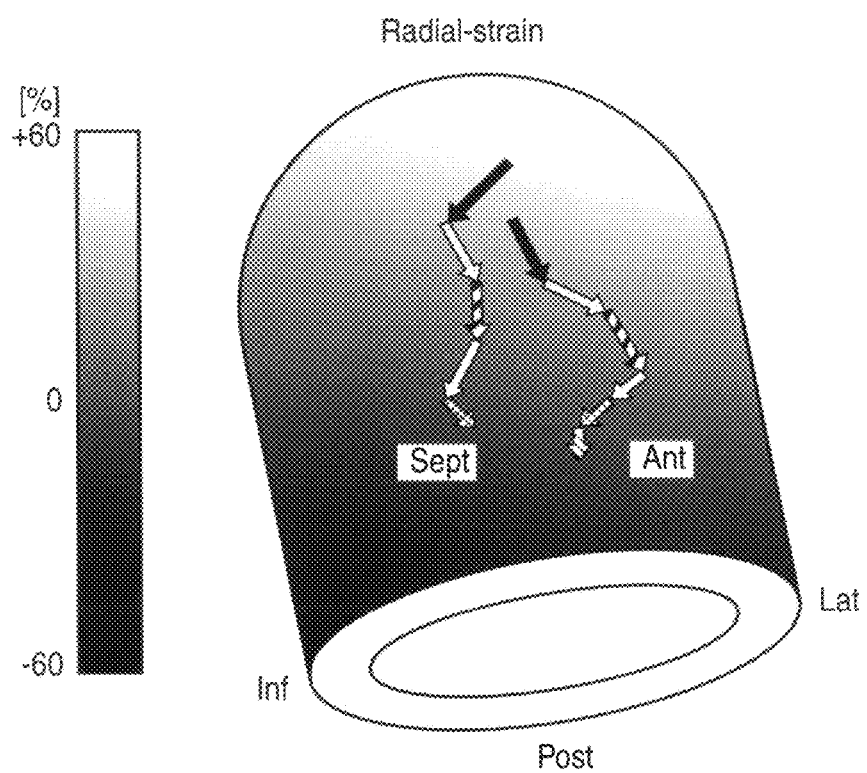
FIG. 4 is a diagram showing a positional example of a display mode of a mapping image (surface rendering image) and excitement propagation information in a display unit 23.
Figure 5:
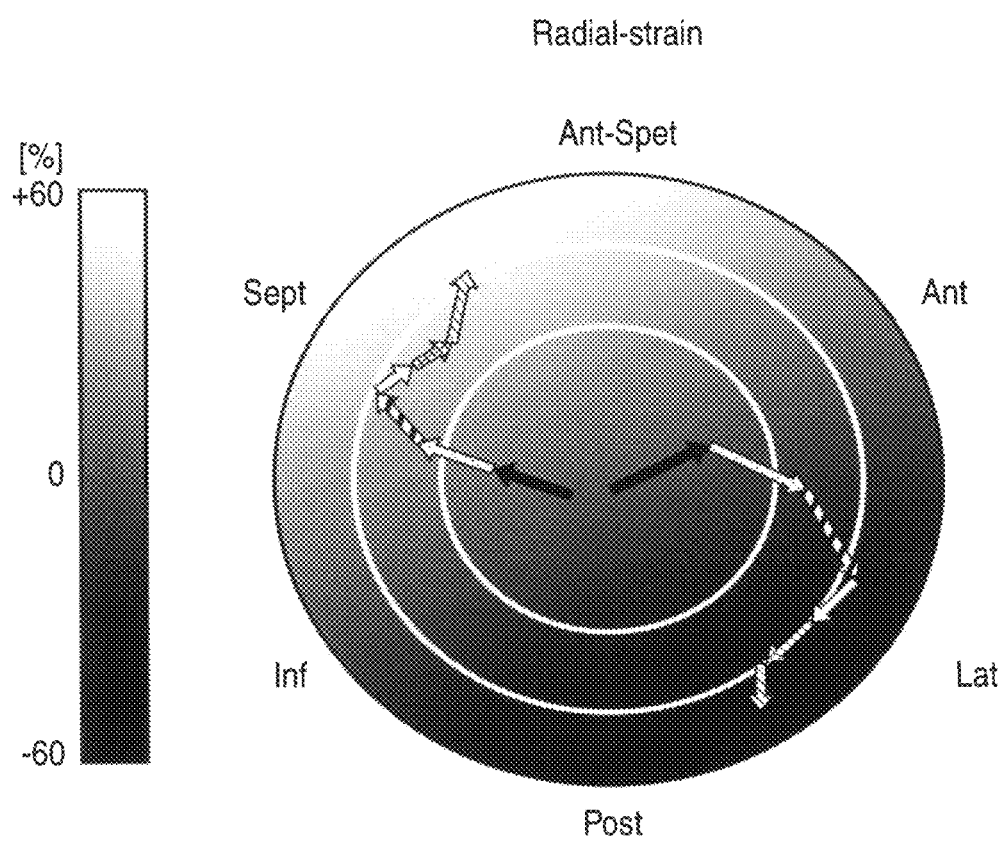
FIG. 5 is a diagram showing an example of a display mode of a mapping image (polar mapping image) and excitement propagation information according to the first embodiment.

FIG. 4 is a diagram showing a positional example of a display mode of a mapping image (surface rendering image) and excitement propagation information in the display unit 23. FIG. 5 is a diagram showing a positional example of a display mode of a mapping image (polar-mapping image) and excitement propagation information in the display unit 23. In the diagrams, the state of the excitement propagation is displayed as a locus line so as to superimpose on a present mapping image and sequentially updated with time. Therefore, by observing the excitement propagation information and the mapping image dynamically displayed, the observer can directly and visually grasp the state of propagation of mechanical excitement of the heart.

The mapping image and the excitement propagation information can be also displayed as a still image on desired time phase as necessary.

In the display of the excitement propagation information and the mapping image, as shown in FIGS. 4 and 5, support information (that is, character information of Sept/Ant/Lat/Post/Inf) for orientating an anatomical segment on the cardiac muscle region in a mapping image can be allocated to a corresponding heart wall position and displayed with a marker.

Association between an image for orientation and an anatomical segment can be realized by, for example, allocating pre-specified sections (such as apical four-chamber image, apical two-chamber image, and the like) as a display format at the time of data collection, and adjusting the probe position in accordance with the display format. By performing such marker display, the observer can observe information indicative of the state of the space-time propagation of the mechanical excitement of the heart while grasping a region anatomically seen in the heart.

(Application 1)

In the excitement propagation information generating function, the velocity of the local peak position can be calculated at time phases together with the locus and displayed so as to be included in the excitement propagation information. The velocity in the local peak position can be calculated on the basis of the motion direction and the motion amount at each time phase and time between frames. The velocity in the local peak position may be displayed as a graph or expressed as a length of a vector which is a locus line corresponding to each time phase.

(Application 2)

Figure 6:
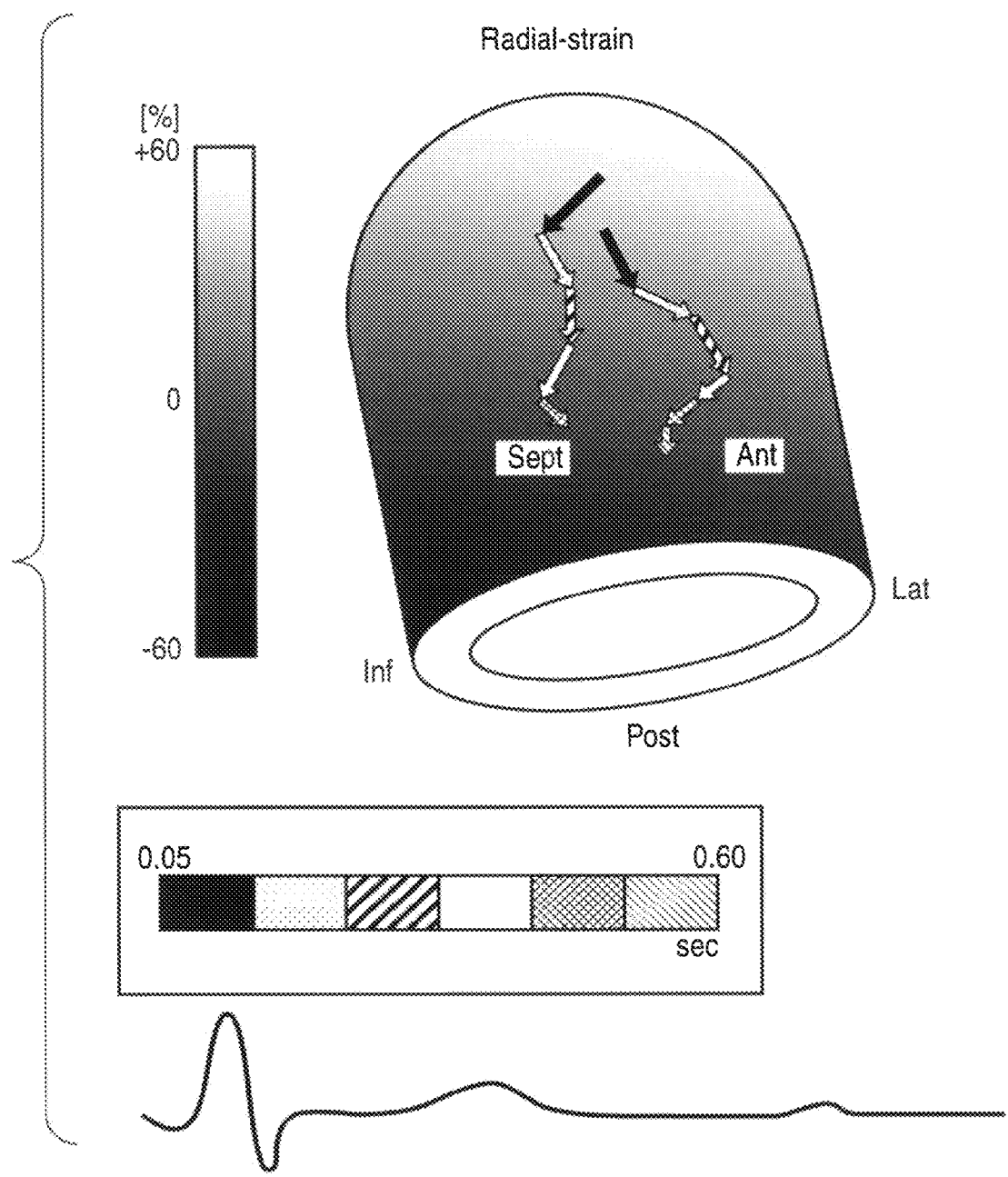
FIG. 6 is a diagram showing a display example in the case of drawing a locus line while assigning different colors to different time phases.

In the excitement propagation information generating function, to obtain correspondence with the heart time phase, it is also possible to assign different colors to the locus line at different time phases and display the locus line in the different colors. For example, as shown in FIG. 6, it is preferable to simultaneously display a color bar indicating correspondence between colors and time phases. In the case of displaying the color bar as described above, as shown in FIG. 6, it is preferable to add display for comparison between electrocardiogram (ECG) waveform and the coloring.

The method of displaying the locus at time phases is not limited to the above example. Any display mode by which a time phase can be discriminated may be employed such as a mode of adding character information indicative of a time phase to every interval of the locus.

(Application 3)

Figure 7:
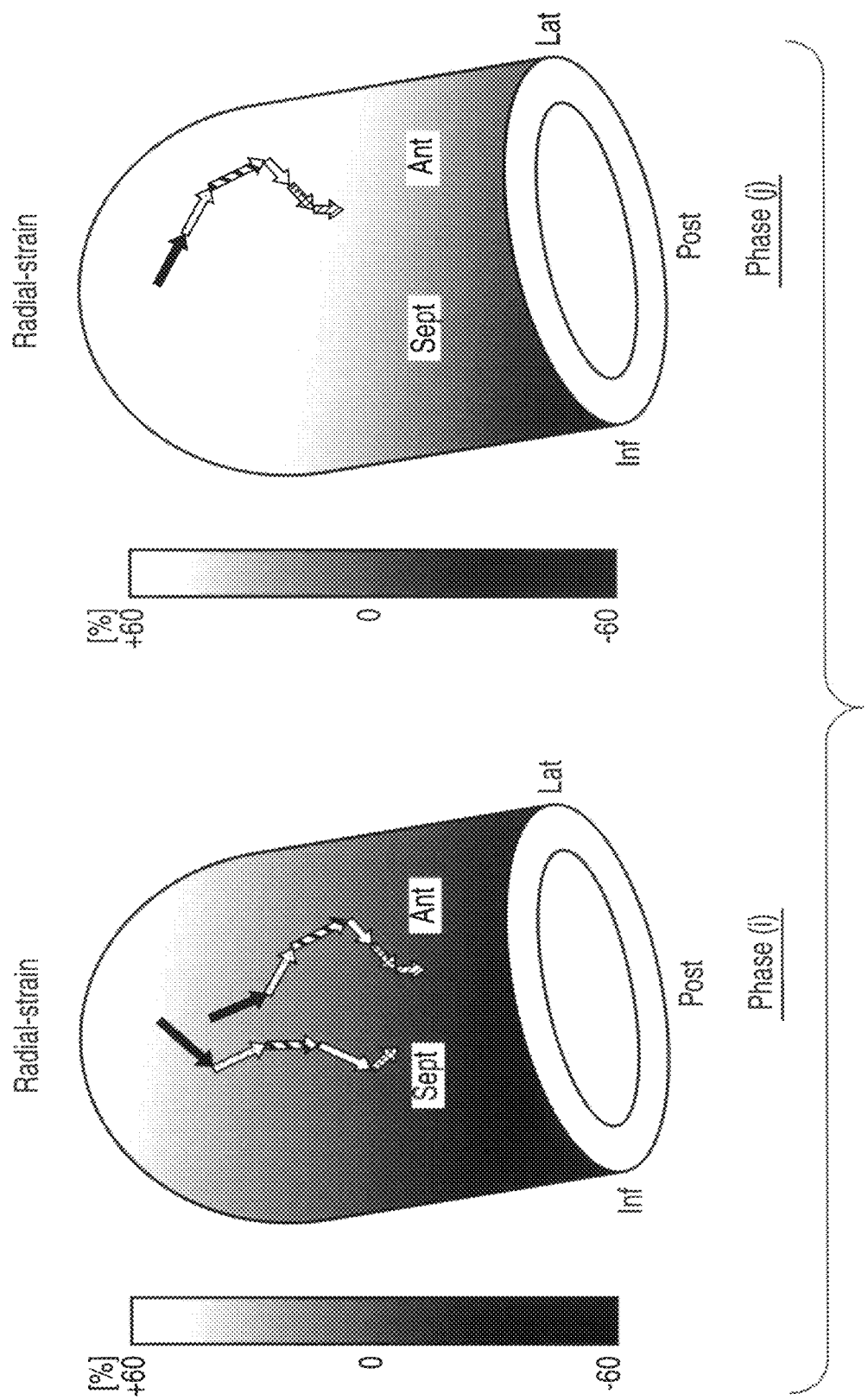
FIG. 7 is a diagram showing another example of the display mode of a mapping image and excitement propagation information according to the first embodiment.

A plurality of pieces of time-series volume data at different times as references (for example, two reference times ti and tj) are collected in step S1. The excitement propagation information generating process in the steps S2 to S4 is executed using the collected data. The excitement propagation information obtained as a result of the process may be concurrently (or alternately) displayed, for example, as shown in FIG. 7. The application 3 is particularly practically useful in the case of observing a situation after a predetermined period, for example, in the case of using one of the time-series volume data groups as data before treatment and the other time-series volume data group as data after treatment, or the case of comparing different time phases at stress echoes (for example, before stress and after stress).

FIG. 7 illustrates the case where both of motion information is a radial strain. The invention is not limited to this case. Different kinds of motion information may be displayed in Phases (i) and (j).

(Application 4)

It is also possible to generate a plurality of different types of motion information (for example, a radial strain and a longitudinal strain) from a single time-series volume data group in step S2, execute the excitation propagation information generating process in the steps S3 an S4 using the different pieces of information, and concurrently (or alternately) display mapping images on which the resultant excitation propagation information is superimposed.

With such a configuration, the observer can promptly and easily see a plurality of different pieces of heart wall motion information and excitement propagation information and three-dimensionally grasp a composite state.

With the above-described configuration, the following effects can be obtained.

By the ultrasonic diagnostic apparatus, a three-dimensional mapping image at each time phase obtained by mapping motion information. The peak value of motion information in a local area at time phases is retrieved. On the basis of the result, a locus line or the like indicative of fluctuations with time of a local peak region is generated. For example, the locus line is displayed so as to be superimposed on a mapping image. The observer can directly grasp the state of space-time propagation of the mechanical excitement of the heart by observing the locus line on the displayed mapping image.

The ultrasonic diagnostic apparatus, as necessary, calculates movement speed at each time phase of a region corresponding to a local peak and can display it so as to be included in the excitement propagation information. Therefore, by observing the movement speed at each time phase included in the excitement propagation information, the observer can quantitatively grasp the state of space-time propagation of the mechanical excitement of the heart.

(Second Embodiment)

A second embodiment of the present invention will be described.

The ultrasonic diagnostic apparatus of the first embodiment traces a region having a local peak value spatial-temporally. Using the result, the state of the space-time propagation of the mechanical excitement of the heart is grasped.

In contrast, an ultrasonic diagnostic apparatus of the second embodiment extracts a region having a value equal to or larger than a reference value (threshold) as a peculiar area without being limited to a local peak value and, using the result, generates excitement propagation information.

The applications described in the first embodiment can be applied also to the ultrasonic diagnostic apparatus of the second embodiment.

Figure 8:
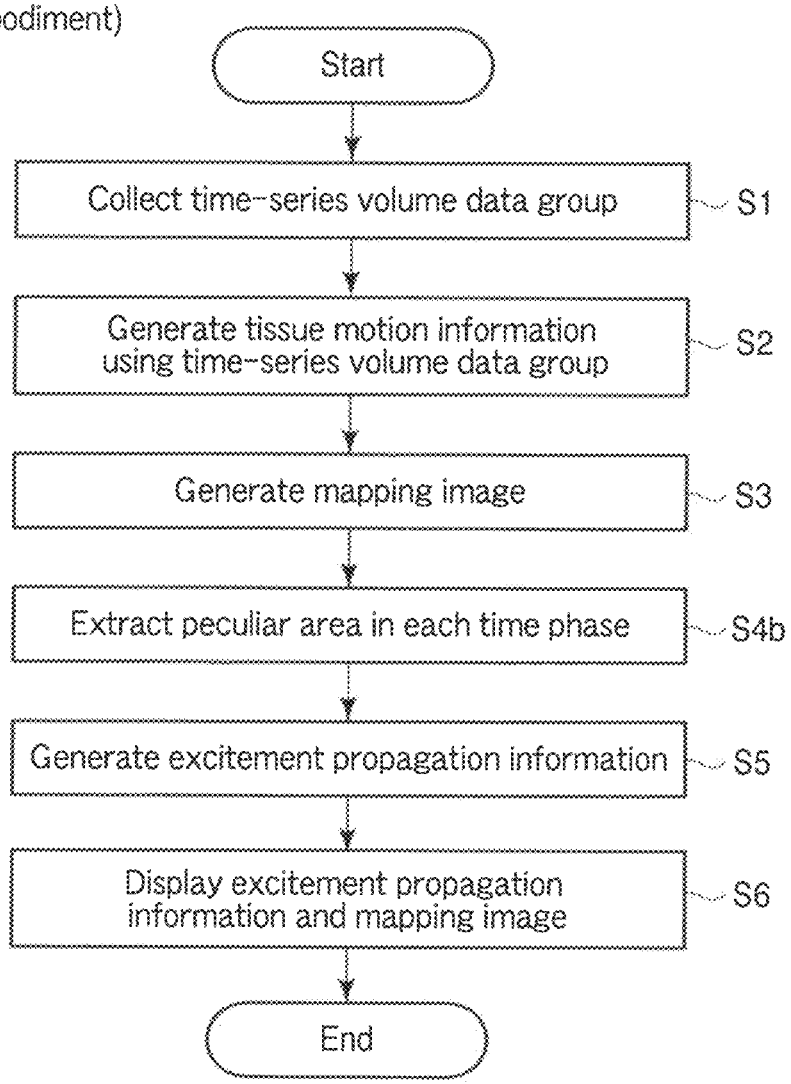
FIG. 8 is a flowchart showing the flow of processes executed in an excitement propagation information generating process according to a second embodiment.

FIG. 8 is a flowchart showing the flow of processes executed in the excitement propagation information generating process of the second embodiment. The processes will be described below.

[Steps S1, S2, and S3]

Steps S1, S2, and S3 are substantially the same as those of the first embodiment.

[Extraction of Peculiar Area: Step S4$b$]

Next, using time-series surface rendering images generated (at time phases), extraction of peculiar areas at time phases is executed (step S4$b$). Specifically, the excitement propagation analyzing unit 38 extracts an area (peculiar area) in which motion information is equal to or larger than a predetermined threshold from a surface rendering image at initial time phase t0 selected by a predetermined method. The excitement propagation analyzing unit 38 similarly extracts a peculiar area in which motion information is equal to or larger than the predetermined threshold from a surface rendering image at the next time phase t1. In such a manner, extraction of peculiar areas is executed on all of time-series surface rendering images.

An example of a method of providing a threshold for use in the peculiar area extracting process is "spatial peak value×$\alpha$" ($0 \leq \alpha 1.0$) at each time phase. For example, $\alpha$ can be set as about 0.9. Naturally, the value $\alpha$ can be arbitrarily set. For example, by increasing $\alpha$, a region around a peak point can be limitedly extracted. By decreasing $\alpha$, the region of a peak area having expansion can be limitedly extracted.

[Generation of Excitement Propagation Information: Step S5]

The excitement propagation analyzing unit 38 generates, as excitement propagation information, fluctuations with time of the extracted peculiar area at the time phases (step S5).

[Display of Excitement Propagation Information and Mapping Image: Step S6]

Subsequently, the control unit 31 controls the display unit 23 so that the excitement propagation information is displayed to be superimposed on the mapping image.

Figure 9:
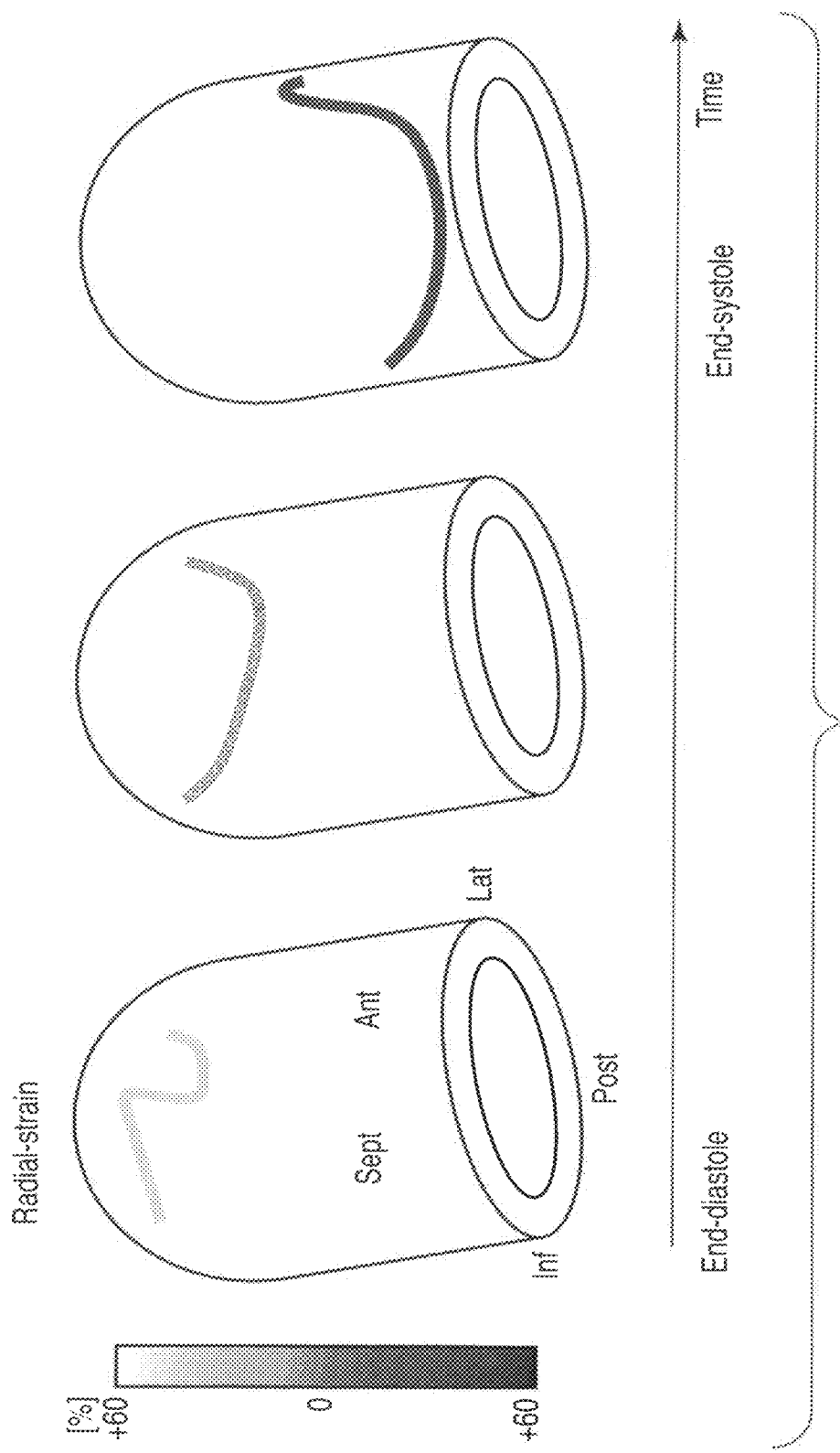
FIG. 9 is a diagram showing an example of a display mode of a mapping image and excitement propagation information according to the second embodiment.
Figure 10:
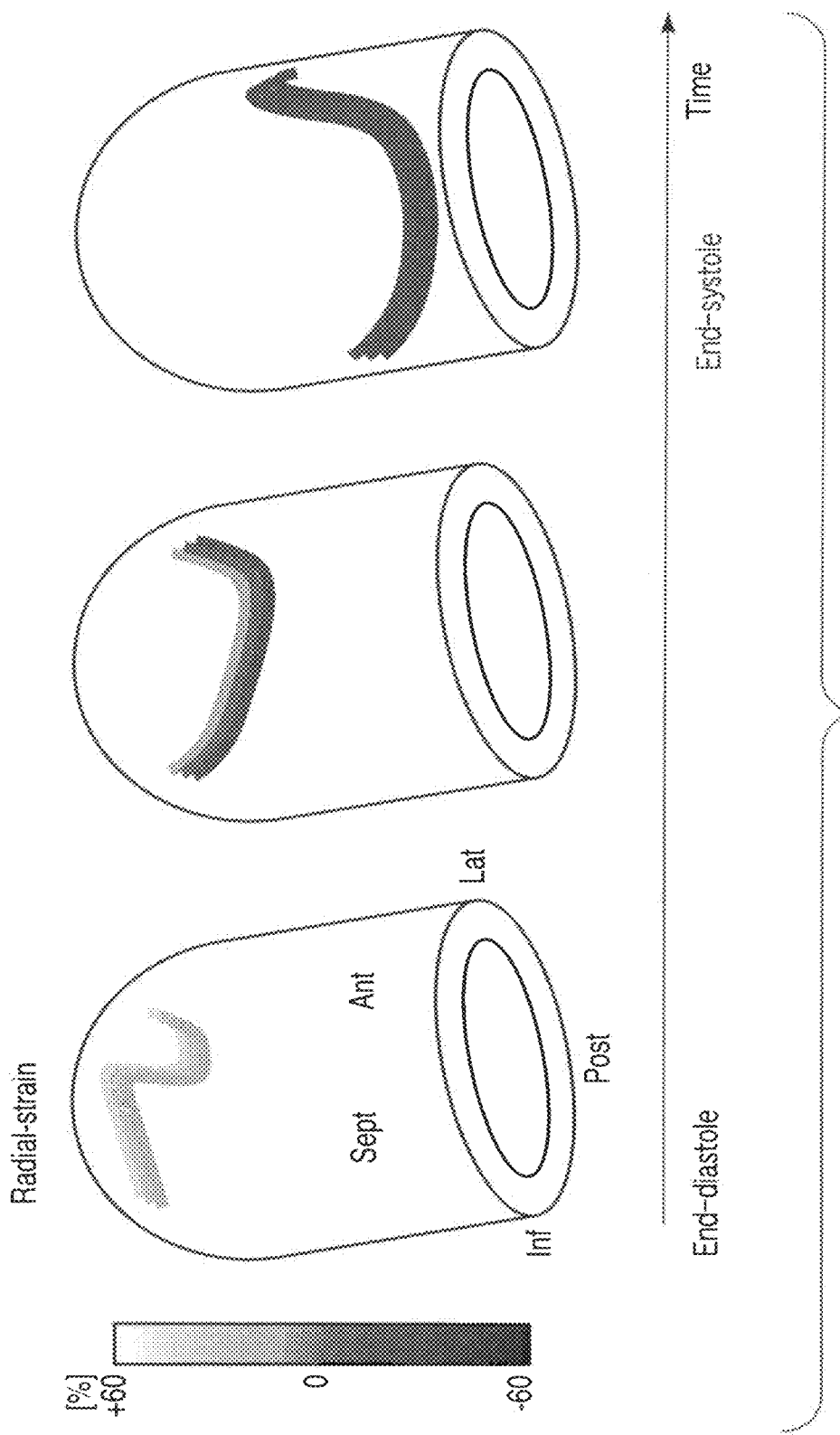
FIG. 10 is a diagram showing another example of the display mode of the mapping image and excitement propagation information according to the second embodiment.

FIG. 9 is a diagram showing an example of a display mode of a mapping image and excitement propagation information in the second embodiment. FIG. 10 is a diagram showing an example of the display mode of the mapping image and excitement propagation information in the case where the value of a is smaller than that in FIG. 9. In each of the diagrams, a peculiar area having motion information of a predetermined value or more is displayed on the present mapping image and is updated with time. Therefore, the observer can directly and visually grasp the state of propagation of mechanical excitement of the heart by observing the excitement propagation information and a mapping image displayed like a motion picture.

With the above-described configuration, the following effects can be obtained.

By the ultrasonic diagnostic apparatus, a region having a value equal to or larger than a reference value on predetermined motion information is extracted as a peculiar area at each of time phases using a three-dimensional mapping image at each time phase obtained by mapping motion information. On the basis of the result, excitation propagation information expressed as fluctuations with time of the peculiar area is generated. For example, the excitation propagation information is displayed so as to be superimposed on a mapping images. The observer can directly grasp the state of space-time propagation of the mechanical excitement of the heart by observing the peculiar area on the displayed mapping image.

The ultrasonic diagnostic apparatus, as necessary, calculates movement speed at each time phase of a peculiar region and can display it so as to be included in the excitement propagation information. Therefore, by observing the movement speed at each time phase included in the excitement propagation information, the observer can quantitatively grasp the state of space-time propagation of the mechanical excitement of the heart.

The present invention is not limited to the foregoing embodiments but can be embodied by modifying the components without departing from the gist in practical phase.

By properly combining a plurality of components disclosed in the embodiments, various inventions can be generated. For example, some components may be deleted from all of the components described in the embodiments. Further, components in different embodiments can be properly combined.

What is claimed is:

1. An ultrasonic image processing method comprising:
generating first tissue motion information in a first period using a first time as a reference, using a first volume data group made of a plurality of pieces of volume data collected in the first period, of cardiac tissue;
generating first time-series tissue motion information images in the first period;
specifying at least one local area in the first time-series tissue motion information images, which has a value equal to or larger than a predetermined threshold obtained by multiplying a spatial peak value at each time phase by a coefficient of less than one, wherein by increasing a value of the coefficient, a region around a peak point is limitedly extracted, and by decreasing the value of the coefficient, a region of a peak area having expansion is limitedly extracted, by searching for fluctuations with time of the local area, in each of the entire tissue motion information images, and generating first three dimensional propagation information using the fluctuations with time, and including information indicative of correspondence between the local area and a time phase; and
displaying the first three dimensional propagation information.

2. The method of claim 1, wherein the generating the first time-series tissue motion information image in the first period comprises performing mapping using either a reconstructing process including volume-rendering or a reconstructing process employing a polar coordinate system using a cardiac apex as a pole and a basal part as a periphery.

3. The method of claim 1, wherein the generating the time-series tissue motion information image in the first period comprises mapping the first tissue motion information to endocardium of the cardiac tissue.

4. The method of claim 1, wherein the information indicative of correspondence between the region having the local peak and the time phase is a locus in time phases of the region having the local peak.

5. The method of claim 4, further comprising displaying the locus while assigning different colors to the time phases.

6. The method of claim 1, further comprising calculating movement speed of the local area in each of time phases, using the first tissue motion information in the first period, and
generating the first three dimensional propagation information including the calculated movement speed.

7. The method of claim 1, further comprising:
generating second tissue motion information in a second period using second time different from the first time as a reference, using a second volume data group made of a plurality of pieces of volume data collected in the second period, of the cardiac tissue,
generating a second time-series tissue motion information image in the second period,
generating second three dimensional propagation information showing a state of space-time propagation of mechanical excitement of the cardiac tissue by using the second time-series tissue motion information image, and
displaying the second three dimensional propagation information and the second time-series tissue motion image concurrently or alternately with the first three dimensional propagation information and the first time-series tissue motion image.

8. The method of claim 7, wherein the first tissue motion information and the second tissue motion information are motion information of a same kind.

9. The method of claim 7, wherein the first tissue motion information and the second tissue motion information are motion information of different kinds.

10. The method of claim 1, further comprising:
generating second tissue motion information in the first period using the first volume data group of the cardiac tissue,
generating a second time-series tissue motion information image in the first period,
generating second three dimensional propagation information showing a state of space-time propagation of mechanical excitement of the cardiac tissue by using the second time-series tissue motion information image, and
displaying the second three dimensional propagation information and the second time-series tissue motion image concurrently or alternately with the first three dimensional propagation information and the first time-series tissue motion image.

11. The method of claim 1, further comprising displaying, together with the tissue motion image, support information for grasping correspondence of an anatomical segment on the tissue.

12. The method of claim 1, wherein the tissue motion information is any of local strain, rotation, twist, torsion and displacement of tissue or, as their time rate of change, any of strain rate, rotation rate, twist rate, torsion rate and velocity.

13. The method of claim 1, further comprising computing movement vector information of a local area of tissue by pattern matching process, and generating motion information of tissue by process including tracking using the movement vector information.

14. The method of claim 1, further comprising generating tissue motion information separated to components in a radial direction of a heart, in a longitudinal direction, and in a circumferential direction.

15. The method of claim 1, further comprising specifying the local area by using a relative threshold which is defined on the basis of a spatial peak value of the tissue motion information.

16. The method of claim 1, further comprising specifying at least one local area where the first tissue motion information has a maximum value or minimum value in an initial time phase in the first period and specifying the at least one local area which the first tissue motion information has a local peak.

17. The method of claim 16, further comprising specifying the at least one local area in a time phase succeeding to an initial time phase based on the at least one local area in the initial time phase and retrieving at least one local area where the first tissue motion information has a maximum value or minimum value.

18. The method of claim 1, wherein the at least one local area corresponds to at least one spatial region of the tissue motion information image at a predetermined time phase.

19. The method of claim 1, further comprising specifying the at least one local area retrieving a peak which is part of the image based on the spatial location of the peak detected in a previous time phase.

20. The method of claim 1, further comprising adopting, as a location of the local area of a current frame, the spatial location having a value of the tissue motion information in the peak in the retrieved at least one local area that exceeds a threshold.

21. An ultrasonic image processing method comprising:
generating tissue motion information of the cardiac tissue over a plurality of time phases using the plurality of pieces of volume data;
specifying at least one peculiar area with a plurality of time phases in the first time-series tissue motion information images, which has a value equal to or larger than a predetermined threshold obtained by multiplying a spatial peak value at each time phase by a coefficient of less than one, wherein by increasing a value of the coefficient, a region around a peak point is limitedly extracted, and by decreasing the value of the coefficient, a region of a peak area having expansion is limited extracted, according to the tissue motion information, in a local area in regard to the tissue motion information; and
displaying and updating the peculiar area with the plurality of time phases, specified by a propagation information generating unit.

* * * * *